United States Patent
Suzuki et al.

(10) Patent No.: US 8,911,827 B2
(45) Date of Patent: Dec. 16, 2014

(54) CHEMICAL VAPOR DEPOSITION METHOD USING AN ORGANOPLATINUM COMPOUND

(75) Inventors: Kazuharu Suzuki, Ibaraki (JP); Shunichi Nabeya, Ibaraki (JP); Masayuki Saito, Ibaraki (JP)

(73) Assignee: Tanka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 14/003,297

(22) PCT Filed: Apr. 16, 2012

(86) PCT No.: PCT/JP2012/060255
§ 371 (c)(1),
(2), (4) Date: Sep. 5, 2013

(87) PCT Pub. No.: WO2012/144455
PCT Pub. Date: Oct. 26, 2012

(65) Prior Publication Data
US 2013/0344243 A1    Dec. 26, 2013

(30) Foreign Application Priority Data
Apr. 20, 2011  (JP) ................. P2011-093671

(51) Int. Cl.
C23C 16/18   (2006.01)
C07F 15/00   (2006.01)

(52) U.S. Cl.
CPC ............. C23C 16/18 (2013.01); C07F 15/0086 (2013.01)
USPC ..................................... 427/250; 427/255.31

(58) Field of Classification Search
USPC ............................................. 427/250, 255.31
See application file for complete search history.

(56) References Cited

U.S. PATENT DOCUMENTS

| | | | |
|---|---|---|---|
| 3,622,367 A | 11/1971 | Haag et al. | |
| 3,635,761 A | 1/1972 | Haag et al. | |
| 5,130,172 A * | 7/1992 | Hicks et al. | 427/584 |
| 5,783,716 A | 7/1998 | Baum et al. | |
| 5,929,267 A | 7/1999 | Kadokura | |
| 6,162,712 A | 12/2000 | Baum et al. | |
| 2001/0036509 A1 * | 11/2001 | Kitada et al. | 427/255.28 |
| 2005/0155552 A1 * | 7/2005 | Kitada et al. | 118/715 |
| 2007/0269981 A1 | 11/2007 | Lavoie | |
| 2014/0065060 A1 * | 3/2014 | Gerlinger et al. | 423/659 |

FOREIGN PATENT DOCUMENTS

| | | |
|---|---|---|
| JP | H11-292889 | 10/1999 |
| JP | 2001-504159 A | 3/2001 |
| JP | 2008-231473 | 10/2008 |

OTHER PUBLICATIONS

Van Asselt, Rob, et al., "Zerovalent Palladium and Platinum Complexes Containing Rigid Bidentate Nitrogen Ligands and Alkenes: Synthesis, Characterization, Alkene Rotation and Substitution Reactions." Inorganic Chemistry, vol. 33, No. 7, 1994, pp. 1521-1531.*

Lee, Sun Sook, et al., "Synthesis of Novel Platinum Precursor and Its Application to Metal Organic Chemical Vapor Deposition of Platinum Thin Films". Bull. Korean Chem. Soc., 2008, vol. 29, No. 8, pp. 1491-1494.*

Xue, Ziling, et al., "Organometallic Chemical Vapor Deposition of Platinum." Chem. Mater. 1992, 4, 162-166.*

Vargas Garcia, J.R., et al., "Chemical Vapor Deposition of Iridium, Platinum, Rhodium and Palladium". Materials Transactions, vol. 44, No. 9 (2003) pp. 1717-1728.*

Mokuolu, Q. F., et al, "Early-late, mixed-metal compounds supported by amidophosphine," Dalton Trans., 2004, No. 13, p. 1960-1970, particularly, p. 1968.

Vaughan, T. F., et al, "Comparison of the Reactivity of Platinum (II) and Platinum (0) Complexes with Iminophosphine and Phosphinocarbonyl Ligands," Organometallics, Oct. 2011, vol. 30, No. 19, p. 5170-5180, particularly, p. 5177.

Cyril Thurier, Pascal Doppelt, "Platinum OMCVD Processes and Precursor Chemistry", Coordination Chemistry Reviews; Elsevier Science, Amsterdam, NL; vol. 252, No. 1-2; Dec. 2007; pp. 155-169.

EP12774783 Supplementary European Search Report, dated Jul. 28, 2014.

* cited by examiner

Primary Examiner — Bret Chen
(74) Attorney, Agent, or Firm — Roberts & Roberts, LLP

(57) ABSTRACT

A chemical deposition method for producing a platinum thin film or a platinum compound thin film by chemical vapor deposition of an organoplatinum compound is represented by the following formula, which includes a divalent platinum atom, and hexadiene or a hexadiene derivative and alkyl anions coordinated to the divalent platinum atom. In the following formula, $R_1$ and $R_2$ are each an alkyl group, and may be different from each other. $R_3$ and $R_4$ are each a hydrogen atom or an alkyl group, and may be different from each other. The organoplatinum compound is satisfactory in stability and generates no toxic substance in film formation, and hence is satisfactory in handleability and excellent in practicability. The organoplatinum compound has a high vapor pressure, enables the film formation at a low temperature, and is useful as a CVD raw material easily forming a film on a spatial structure.

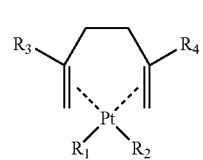

[Formula 1]

10 Claims, No Drawings

CHEMICAL VAPOR DEPOSITION METHOD USING AN ORGANOPLATINUM COMPOUND

BACKGROUND OF THE INVENTION

1. Field of the Invention

The present invention relates to an organoplatinum compound used as a raw material for producing a platinum thin film or a platinum compound thin film by a chemical vapor deposition method such as a CVD method or an ALD method. Specifically, the present invention relates to an organoplatinum compound having a high vapor pressure and being capable of forming a platinum thin film even at a low temperature of 350° C. or lower.

2. Description of the Related Art

As an electrode material for a field effect transistor (FET) incorporated into an integrated circuit, a solid type Ni—Pt silicide electrode having a three-dimensional structure is known. In the solid type Ni—Pt silicide electrode, a spatial structure is adopted for ensuring the surface area in spite of being high in density due to the miniaturization of the FET, and Pt is added for improving the thermal stability of the Ni silicide electrode. In the production of the Ni—Pt silicide electrode having a spatial structure, it is required to form a Pt thin film and a Ni thin film on the Si having a spatial structure produced beforehand. In this case, it is required to cover the Pt thin film and the Ni thin film electrode so as to follow the shapes thereof uniformly and in the same proportion.

As the method for producing a platinum thin film, the PVD method such as a sputtering method can be applied; however, it is difficult for the PVD method to cover an electrode having a spatial structure uniformly. Accordingly, it can be said that promising is the application of the chemical vapor deposition method such as the CVD method excellent in step coverage (level difference coverage). It is also expected that the use of the metal thin film such as the Ni—Pt silicide thin film even in the gate electrode of the FET enables the miniaturization of devices and the achievement of high performance of devices. In this case, the use of the conventional sputtering method in the fabrication of the metal electrode causes damages in devices, and hence it is necessary to form a metal thin film under physically moderate conditions. When the application of the chemical vapor deposition method such as the CVD method enables the film formation at a low temperature, the production of such devices is also enabled.

As the raw material for producing a platinum thin film or a platinum compound thin film with the CVD method, a large number of compounds have hitherto been known. Examples of such a compound include bis(acetylacetonato)platinum(II) complex (Patent Literature 1), cyclopentadienyl trimethylplatinum(IV) complex (Patent Literature 2), and tetrakis(trifluorophosphine)platinum compound (Patent Literature 3).

[Formula 1]

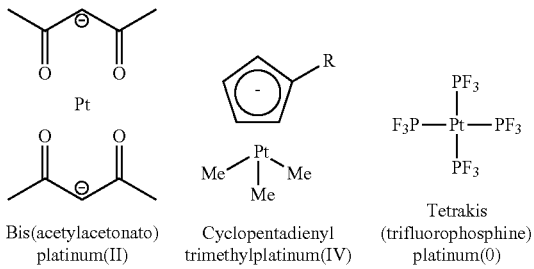

Bis(acetylacetonato) platinum(II)  Cyclopentadienyl trimethylplatinum(IV)  Tetrakis (trifluorophosphine) platinum(0)

PRIOR ART DOCUMENTS

Patent Literature

Patent Literature 1: National Publication of International Patent Application No. 2001-504159
Patent Literature 2: Japanese Patent Application Laid-Open No. Hei 11-292889
Patent Literature 3: Japanese Patent Application Laid-Open No. 2008-231473

SUMMARY OF THE INVENTION

Problems to be Solved by the Invention

Generally, a raw material for CVD is required to have a high vapor pressure and a low decomposition temperature so as to allow the film formation temperature to be reduced, for stably forming the film. In particular, in the case of an FET, it is important to perform the film formation at a low temperature for maintaining the performances of the device. The foregoing conventional platinum compounds can also be regarded to have these properties, though not quite satisfactorily. However, for forming the foregoing electrode having a spatial structure, more strict standards are required for these properties. For example, with respect to the vapor pressure, when a uniform film is formed on an electrode made to have a solid shape, it is effective to enable a high concentration feeding of a raw material gas, and for that purpose, a substance having a higher vapor pressure is preferable. Also, with respect to the decomposition temperature, the decomposition temperature is preferably a low temperature for rapidly forming a film from a high concentration raw material gas while the damage of the substrate (electrode) is being suppressed.

Among the foregoing platinum compounds, tetrakis(trifluorophosphine)platinum(0) complex enables a film formation at a lower temperature, but is unstable not only against air or humidity but also against light or heat, and hence is required to be stored at a low temperature. Moreover, tetrakis(trifluorophosphine)platinum(0) complex generates $PF_3$ having stronger toxicity at the time of the film formation or due to decomposition. Also, for stabilizing the vapor content and thus obtaining a uniform film satisfactory in level difference coverage, it is necessary in some cases to use PF3, a ligand, in order to maintain the stability in the gas state before the film formation.

The necessity of forming a platinum film on a substrate or a base material having a spatial structure is found, in addition to the case of the foregoing Pt—Ni electrode of an FET, for example, in the examples of thin film formation in the platinum catalyst thin film for electric cell such as the platinum catalyst for a fuel cell and the platinum catalyst for a dye-sensitized solar cell, and thus there is much demand for such a platinum film formation. The present invention has been achieved under the foregoing background, and provides a platinum compound for a CVD raw material, having a high vapor pressure, being capable of forming a film at a low temperature, being easy in forming a film on a spatial structure, and being excellent in stability and handleability.

Means for Solving the Problems

The present invention for solving the foregoing problem is an organoplatinum compound for producing a platinum thin film or a platinum compound thin film by a chemical vapor deposition method, wherein the organoplatinum compound is represented by the following formula, and includes a divalent platinum atom, and hexadiene or a hexadiene derivative and alkyl anions coordinated to the divalent platinum atom.

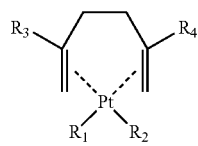

[Formula 2]

(In the formula, the substituents $R_1$ and $R_2$ are each an alkyl group. $R_1$ and $R_2$ may be different from each other. $R_3$ and $R_4$ are each a hydrogen atom or an alkyl group. $R_3$ and $R_4$ may be different from each other.)

The platinum compound according to the present invention includes a divalent platinum atom and hexadiene or a derivative thereof and alkyl anions coordinated as ligands to the divalent platinum atom. The present inventors have conceived of these platinum compounds on the basis of the following reasons involving the structures constituted with the central metal atom and the ligands coordinated to the central metal atom.

The diene as a ligand is an electrically neutral π-bonding type ligand having no charge in each of the portions bonded to the metal atom. Being electrically neutral means being weak in the bonding strength with the metal, and thus a complex easily undergoing thermal decomposition at a low temperature is obtained. The diene as a ligand has a relatively small molecular weight (molecular weight of hexadiene: 82.14) and a relatively low boiling point (boiling point of hexadiene: 60° C.), and hence has advantages of being easily evaporated after decomposition and of hardly remaining as an impurity in the metal film.

The alkyl anions as another type of ligands can increase the vapor pressure of the complex by appropriately setting the molecular weights of the alkyl anions. The alkyl anions can be released as hydrocarbons having low boiling points by performing the film formation and decomposing the complex in a reducing atmosphere or a hydrogen gas atmosphere. Because of this, the alkyl anions hardly become residual impurities in the deposited metal film, and hence is suitable as the ligands for releasing pure metal.

With respect to platinum to be the central metal, most of platinum complexes including, as the central metal, divalent or tetravalent platinum having a positive charge are stable; however, the present inventors regard as preferable the divalent platinum complexes having an appropriate stability because the easiness in the handling of the compounds in the course of synthesis, purification, and storage is also important.

On the basis of the foregoing reasons, the platinum complex according to the present invention is specified to be the platinum complex including a divalent platinum atom and hexadiene or a derivative thereof and alkyl anions coordinated as ligands to the divalent platinum atom.

The two alkyl anions $R_1$ and $R_2$ coordinated to a platinum atom are each preferably any one of a methyl group, an ethyl group and a propyl group. These alkyl anions each have a small molecular weight, and hence can suppress the decrease of the vapor pressure associated with the increase of the molecular weight when the complex is formed. Also, because the stability of the platinum complex tends to decrease with the increase of the carbon chain length of the alkyl group, the synthesis or handling of the complex including as ligands long chain alkyl groups having 4 or more carbon atoms comes to be difficult. A methyl group is particularly preferable among alkyl groups. This is because a methyl group becomes methane having a low boiling point (boiling point of methane: −162° C.) after the decomposition of the complex, and hence the methyl group can be released without leaving any impurity in the formed metal thin film.

The inclusion, as the ligands to platinum, of the derivatives of hexadiene in addition to hexadiene is for allowing the film formation temperature to be a low temperature while the stability of the platinum complex is being ensured, according to the two alkyl anions to be coordinated. In other words, as the two alkyl anions ($R_1$ and $R_2$) to be coordinated to platinum are changed over to the substituents having larger molecular weights such as ethyl groups or propyl groups, the stability of the platinum complex is decreased so as for the platinum complex to be decomposed at a temperature of about the same as room temperature, and consequently the handleability of the platinum complex as the CVD raw material is affected. Accordingly, while the stability of the whole platinum complex is being maintained by varying the coordination strength of the ligand through introducing substituents into hexadiene as the other ligand, the decomposition properties of the platinum complex at the time of the film formation is allowed to be satisfactory.

Preferable specific examples of the platinum complex according to the present invention include the following compounds.

(i) An organoplatinum compound with the substituents $R_1$ and $R_2$ being each a methyl group, and the substituents $R_3$ and $R_4$ being each a hydrogen atom.

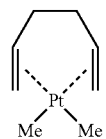

[Formula 3]

1,5-Hexadiene-dimethylplatinum (ii) Organoplatinum compounds with the substituents $R_1$ and $R_2$ being each any one of a methyl group, an ethyl group and a propyl group and being the same as each other, and one of the substituents $R_3$ and $R_4$ being a methyl group.

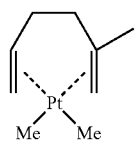 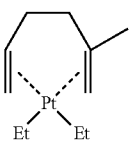

2-Methyl-1,5-hexadiene-dimethylplatinum    2-Methyl-1,5-hexadiene-diethylplatinum

[Formula 4]

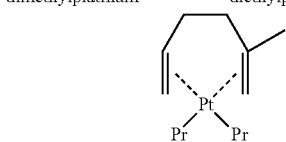

2-Methyl-1,5-hexadiene-dipropylplatinum (iii) Organoplatinum compounds with the substituents $R_1$ and $R_2$ being each any one of a methyl group, an ethyl group and a propyl group and being the same as each other, and both of the substituents $R_3$ and $R_4$ being methyl groups.

[Formula 5]

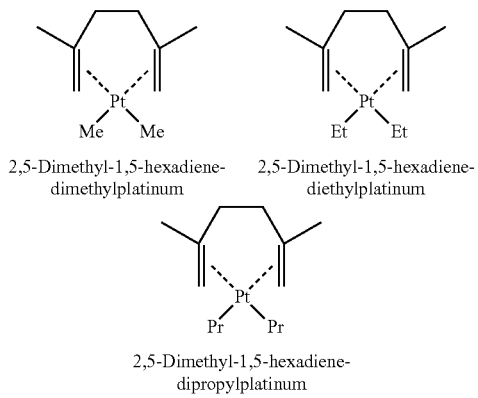

2,5-Dimethyl-1,5-hexadiene-dimethylplatinum 2,5-Dimethyl-1,5-hexadiene-diethylplatinum 2,5-Dimethyl-1,5-hexadiene-dipropylplatinum The method for producing an organoplatinum compound according to the present invention can produce an organoplatinum compound with use of a platinum salt as a starting raw material, and by allowing hexadiene (1,5-hexadiene) or a hexadiene derivative (such as 2-methyl-1,5-hexadiene or 2,5-methyl-1,5-hexadiene) and an alkyl anion salt to sequentially react with the platinum salt. Examples of the usable platinum salt include chloroplatinates (such as $K_2PtCl_4$).

The organoplatinum compound according to the present invention is useful for the formation of the platinum thin film by the CVD method. In the method for forming a thin film, the organoplatinum compound to be a raw material compound is vaporized to prepare a reaction gas, the resulting reaction gas is introduced onto the surface of a substrate, and the organoplatinum compound is decomposed to deposit platinum.

The reaction atmosphere for the decomposition of the organoplatinum compound is preferably a reducing atmosphere; this is because for the solid-type electrode of an FET, the formation of the nickel thin film as well as the platinum thin film is required and the suppression of the oxidation of the thin films is required. Specifically, the introduction of hydrogen or ammonia as the reaction gas is preferable.

An object of the present invention is to allow the film formation temperature to shift toward lower temperatures. From this viewpoint, the heating temperature for the film formation reaction is preferably set at 200° C. to 350° C. This is because when the heating temperature is lower than 200° C., it is difficult to allow the film formation reaction to proceed and it is difficult to obtain a necessary film thickness. This is also because when the heating temperature exceeds 350° C., it is difficult to form a uniform film on an electrode made to have a solid shape, and additionally, it is difficult to maintain the performances of the FET device.

Advantageous Effects of Invention

As described above, the platinum complex according to the present invention has a high vapor pressure and a low decomposition temperature, and hence enables the formation of a platinum thin film at a low temperature. The platinum complex according to the present invention also enables the film formation on a spatial structure. The organoplatinum compound according to the present invention can also be applied to chemical vapor depositions such as the atomic layer deposition method (ALD method) other than the CVD method.

DETAILED DESCRIPTION OF THE PREFERRED EMBODIMENTS

First Embodiment

The present embodiment produced a platinum complex with two coordinated methyl groups as alkyl anions being ligands and coordinated hexadiene as the other ligand (a platinum complex with the substituents $R_1$ and $R_2$ being each a methyl group and the substituents $R_3$ and $R_4$ being each a hydrogen atom: 1,5-hexadienedimethylplatinum(II) (hereinafter, referred to as HDMP)). The reaction formula of the synthesis of HDMP is as follows. Hereinafter, for each stage, the production steps are described.

[Formula 6]

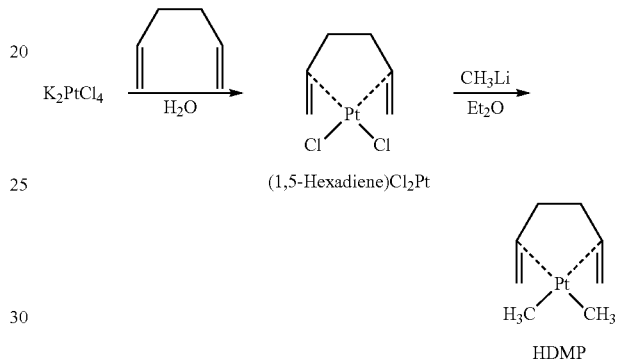

(1,5-Hexadiene)Cl$_2$Pt

HDMP

First, to a solution prepared by dissolving 100.00 g (0.241 mol) of potassium chloroplatinate ($K_2PtCl_4$) in 800 mL of water, 30.00 g (0.365 mol) of 1,5-hexadiene was added. Additionally, to the resulting solution, 50 mL of acetic acid was added in order to allow hexadiene to be mixed with the aqueous phase and was stirred with a mechanical stirrer (200 rpm). The resulting reaction solution was maintained at a constant temperature in an oil bath and stirred in a stepwise manner (the reaction solution was stirred at 25° C. for 2 hours and at 35° C. for 12 hours). In this reaction process, a white precipitate was generated and deposited, and the reaction solution turned pale yellow. Successively, 3.00 g (0.037 mol) of hexadiene was further added, and again stirred in an oil bath in a stepwise manner (the reaction solution was stirred at 45° C. for 3 hours and at 50° C. for 20 hours). After the foregoing reaction, the reaction solution turned nearly transparent, and a white precipitate was obtained. The white precipitate was suction filtrated and collected, washed twice with water, ethanol and diethyl ether, respectively, and air-dried and vacuum dried, to yield 78.33 g (0.225 mol) of white 1,5-hexadiene-platinum(II) dichloride (yield: 93.4%).

Next, the air in a 1-L four-necked flask was replaced with argon gas, and in this flask, 20 g ($5.74 \times 10^{-2}$ mol) of the above-produced 1,5-hexadieneplatinum(II) dichloride and 550 mL of dry diethyl ether were placed, and cooled to −30° C. To the solution, 145 mL of a 1.07 M methyllithium ($CH_3Li$) solution was dropwise added over 45 minutes. Then, the solution was increased in temperature to room temperature while being continuously stirred overnight, and the obtained reaction solution (black) was cooled with ice water. To the cooled reaction solution, 50 mL of a water-ethanol (4:1) mixed solution was dropwise added with a dropping funnel over 30 minutes. Then, the black precipitate was removed with suction filtration, the diethyl ether layer was collected and evaporated, the obtained substance was dissolved in hexane and filtrated through a column chromatography (alumina/hexane), and then the solvent was evaporated from the obtained filtrate. The obtained black liquid was purified by sublimation (heating temperature: 38 to 46° C., cooling temperature: 5° C., pressure: 68 to 84 Pa, 8 hours) to yield 9.06 g ($2.95 \times 10^{-2}$ mol) of HDMP (yield: 51%) as a white solid.

Second Embodiment

The present embodiment produced a platinum complex with two coordinated methyl groups as alkyl anions being ligands and coordinated 2-methyl-1,5-hexadiene as the other ligand (a platinum complex with the substituents $R_1$ and $R_2$ being each a methyl group and the substituent $R_3$ being a hydrogen atom and the substituent $R_4$ being a methyl group: 2-methyl-1,5-hexadienedimethylplatinum(II) (hereinafter, referred to as Me-HDMP)). The reaction formula of the synthesis of Me-HDMP is as follows. Hereinafter, for each stage, the production steps are described.

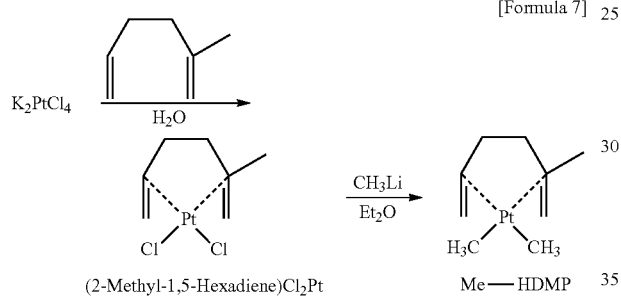

[Formula 7]

First, to a solution prepared by dissolving 20.14 g ($4.85 \times 10^{-2}$ mol) of potassium chloroplatinate ($K_2PtCl_4$) in 160 mL of water, 7.30 g ($7.59 \times 10^{-2}$ mol) of 2-methyl-1,5-hexadiene was added. To the resulting solution, 10 mL of acetic acid was added, and the resulting reaction solution was maintained at a constant temperature while being stirred with a stirrer in an oil bath and stirred in a stepwise manner (the reaction solution was stirred at 35° C. for 31 hours, at 40° C. for 20 hours and at 50° C. for 6 hours). In this reaction process, the reaction solution became nearly transparent, and a white precipitate was obtained. The white precipitate was suction filtrated and collected, washed twice with water, ethanol and diethyl ether, respectively, and air-dried and vacuum dried, to yield 14.14 g ($3.90 \times 10^{-2}$ mol) of white 2-methyl-1,5-hexadieneplatinum(II) dichloride (yield: 80%).

Next, the air in a 500-mL three-necked flask was replaced with argon gas, and in this flask, 12.00 g ($3.31 \times 10^{-2}$ mol) of the above-produced 2-methyl-1,5-hexadieneplatinum(II) dichloride and 200 mL of dry diethyl ether were placed, and cooled to −70° C. To the solution, 84 mL of a 1.07 M methyllithium ($CH_3Li$) solution was dropwise added over 45 minutes. Then, the solution was increased in temperature to room temperature while being continuously stirred overnight, and the obtained reaction solution (black) was cooled with ice water. To the cooled reaction solution, 25 mL of a water-ethanol (4:1) mixed solution was dropwise added with a dropping funnel over 20 minutes. Then, the black precipitate was removed by suction filtration, the diethyl ether layer was collected and evaporated, the obtained substance was dissolved in hexane and filtrated by a column chromatography (alumina/hexane), and then the solvent was evaporated from the obtained filtrate. The obtained black liquid was purified by sublimation (heating temperature: 36 to 39° C., cooling temperature: 15° C., pressure: 50 to 60 Pa, 11 hours) to yield 6.45 g ($2.01 \times 10^{-2}$ mol) of Me-HDMP (yield: 61%) as a white solid.

Third Embodiment

The present embodiment produced a platinum complex with two coordinated methyl groups as alkyl anions being ligands and coordinated 2,5-dimethyl-1,5-hexadiene as the other ligand (a platinum complex with the substituents $R_1$ and $R_2$ being each a methyl group and the substituents $R_3$ and $R_4$ being each a methyl group: 2,5-dimethyl-1,5-hexadienedimethylplatinum(II) (hereinafter, referred to as 2Me-HDMP)). The reaction formula of the synthesis of 2Me-HDMP is as follows. Hereinafter, for each stage, the production steps are described.

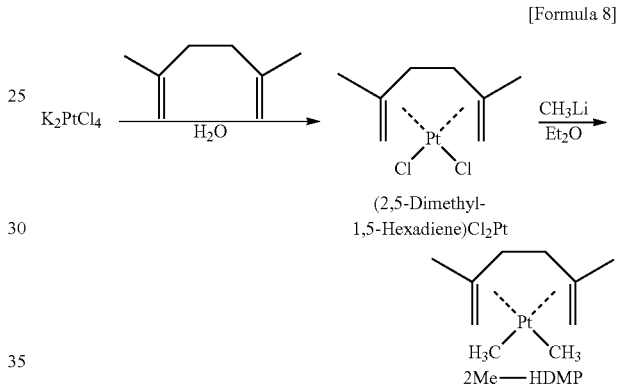

[Formula 8]

First, to a solution prepared by dissolving 20.00 g ($4.82 \times 10^{-2}$ mol) of potassium chloroplatinate ($K_2PtCl_4$) in 160 mL of water, 7.69 g ($6.98 \times 10^{-2}$ mol) of 2,5-dimethyl-1,5-hexadiene was added. To the resulting solution, 20 mL of acetic acid was added, and the resulting reaction solution was maintained at a constant temperature while being stirred with a stirrer in an oil bath and stirred in a stepwise manner (the reaction solution was stirred at 35° C. for 44 hours, at 40° C. for 20 hours, at 50° C. for 9 hours and at 65° C. for 16 hours). In this reaction process, the reaction solution became nearly transparent, and a brown precipitate was obtained. The precipitate was suction filtrated and collected, washed twice with water, ethanol and diethyl ether, respectively, and air-dried and vacuum dried, to yield 14.77 g ($3.93 \times 10^{-2}$ mol) of brown 2,5-dimethyl-1,5-hexadieneplatinum(II) dichloride (yield: 81%).

Next, the air in a 500-mL three-necked flask was replaced with argon gas, and in this flask, 12.00 g ($3.19 \times 10^{-2}$ mol) of the above-produced 2,5-dimethyl-1,5-hexadieneplatinum(II) dichloride and 200 mL of dry diethyl ether were placed, and cooled to −70° C. To the solution, 76 mL of a 1.14 M methyllithium ($CH_3Li$) solution was dropwise added over 45 minutes. Then, the solution was increased in temperature to room temperature while being continuously stirred overnight, and the obtained reaction solution (black) was cooled with ice water. To the cooled reaction solution, 20 mL of a water-ethanol (4:1) mixed solution was dropwise added with a dropping funnel over 20 minutes. Then, the black precipitate was removed by suction filtration, the diethyl ether layer was collected and evaporated, the obtained substance was dissolved in hexane and filtrated by a column chromatography (alumina/hexane), and then the solvent was evaporated from the obtained filtrate. The obtained black liquid was purified by sublimation (heating temperature: 55° C., cooling temperature: 15° C., pressure: 50 to 70 Pa, 9 hours) to yield 6.15 g ($1.83 \times 10^{-2}$ mol) of 2Me-HDMP (yield: 57%) as a white solid.

Evaluation of physical properties of platinum complex: The evaluation of the physical properties of the platinum complexes produced in the first to third embodiments on the basis of TG-DTA was performed. The analysis observed the weight change of each of the platinum complex samples when being heated in a flow of argon gas (200 mL/min), at a temperature increase rate of 3° C./min.

The weight change behaviors of the individual platinum complexes were similar to each other. Specifically, the weight loss slowly started from around 60° C., the loss magnitude drastically increased at around 100° C., namely, the decomposition initiation temperature, and came to an end at around 150° C. Then, heating was continued up to 500° C., but no weight decrease was observed during the course of the heating, and the weight value at around 150° C. remained maintained. A white powder having metal luster remained on the planchet after the completion of the measurement; the white powder is considered to be metallic platinum produced by the thermal decomposition of the platinum complex at the time of the TG-DTA measurement. From this result, it can be understood that each of the platinum complexes is decomposed and deposits metallic platinum by heating even in an argon atmosphere, the thermal decomposition is completed at around 150° C., and the deposition of the pure metal elementary substance easily occurs from the complex. The details of the decomposition initiation temperatures of the respective platinum complexes were as follows: 98.9° C. (HDMP), 98.2° C. (Me-HDMP) and 95.2° C. (2Me-HDMP).

The weight values of the respective samples after the TG-DTA measurement were as follows in relation to the initial weights of the samples: 35.73% (HDMP), 47.62% (Me-HDMP) and 52.63% (2Me-HDMP). The theoretical platinum contents of the respective platinum complexes are 63.48% (HDMP), 60.71% (Me-HDMP) and 58.17% (2Me-HDMP), and hence it can be inferred that during the TG-DTA measurement, the platinum complexes were partially sublimed and/or evaporated. Here, if the white powder remaining after the measurement as described above is assumed to be pure platinum metal, the difference from the theoretical content can be estimated to be the weight of the platinum scattered by sublimation of the platinum complex. This means that 43.71% (HDMP), 21.56% (Me-HDMP) and 9.52% (2Me-HDMP) of the platinum complexes in relation to the initial weights were sublimed.

Although the TG-DTA measurement was performed under the condition of atmospheric pressure, a considerable amount (43.71%) of HDMP was scattered by sublimation. This result suggests that HDMP is a substance having a high vapor pressure and being easily evaporated. The sublimation amounts of Me-HDMP and 2Me-HDMP were smaller than the sublimation amount of HDMP (21.56% (Me-HDMP) and 9.52% (2Me-HDMP)). This is considered to be ascribable to the following two reasons: one reason is such that the molecular weights of Me-HDMP and 2Me-HDMP are larger than the molecular weight of HDMP, and the other reason is such that as can be seen from a comparison of the decomposition initiation temperatures, Me-HDMP and 2Me-HDMP more easily undergo thermal decomposition than HDMP. However, the sublimation amounts observed in this case are the values obtained by the measurement based on TG-DTA under atmospheric pressure. Under a reduced pressure, which is a usual film formation condition, it is possible to generate vapor at a temperature lower than the decomposition point, and hence it is possible to generate vapor under a stable condition involving no thermal decomposition.

The respective produced platinum complexes were stored in the atmosphere at room temperature for one month; however, no change of the platinum complexes such as discoloration was found. In other words, these compounds are extremely stable at room temperature and can be stored in the air.

The melting points of the respective platinum complexes were found to be 35° C. for HDMP, 31° C. for Me-HDMP and 49° C. for 2Me-HDMP. The melding point of Me-HDMP in which one of the substituents in hexadiene is a methyl group is lower than the melting point of HDMP. This is considered to be ascribable to the decrease of the melting point due to the lower molecular symmetry of Me-HDMP than the molecular symmetry of HDMP. The fact that the melting point of 2Me-MHDMP in which both of the substituents in hexadiene are methyl groups is higher than the melting point of HDMP is considered to be ascribable to the molecular weight increased by the introduction of two methyl groups into hexadiene although 2Me-MHDMP and HDMP are equivalent in molecular symmetry. These platinum complexes can be stored in solid state at the time of storage (room temperature), and can be furthermore stably stored as compared to the storing in liquid state. These platinum complexes are easily melted to be liquid by heating at the time of forming a film, and hence it is possible to use a bubbler-type vaporization apparatus capable of performing stable generation of vapor.

Film formation test: A film formation test of platinum thin film was performed with the CVD method with use of each platinum complex as the raw material compounds. As a film formation apparatus, a cold wall-type apparatus was used in which only the substrate stage in the chamber was heated. The carrier gas (nitrogen) for carrying the vapor of a raw material compound onto the substrate is controlled so as to have a constant flow rate with a mass flow controller. For facilitating the deposition of the metal by promoting the decomposition of the raw material compound, the reaction gas (hydrogen) was blown onto the substrate at a constant flow rate with use of a mass flow controller.

The platinum thin film was formed on a substrate (15 mm×15 mm) prepared by depositing a silicon oxide film on a silicone substrate with use of tetraethoxysilane (TEOS). The film formation conditions are as follows.

Sample heating temperature: 40° C.
Substrate heating temperature: 200, 225, 250, 275 and 300° C.
Carrier gas (nitrogen) flow rate: 10 sccm
Reaction gas (hydrogen) flow rate: 50 sccm
Pressure: 50 Pa
Film formation time: 30 minutes The film formation test was performed at each of the foregoing temperatures, and any one of the platinum complex raw materials allowed a platinum thin film to be produced at each of all the foregoing temperatures. The produced platinum thin films each have white metallic luster, and in each of the produced platinum thin films, only the peak derived from platinum was observed and no peaks derived from the impurities such as carbon were observed from the measurement based on XPS. In other words, these platinum thin films were verified to be pure platinum metal films. The platinum thin films were observed with a SEM, and it was verified that the thickness of each of the platinum thin films was 100 nm and the surface of each of the thin films was smooth and had a roughness of 1 nm or less.

The specific resistances of the produced platinum thin films were measured by the four-probe method, and were all found to be 25 μΩcm or less. As compared to the specific resistance (10.5 μΩcm (20° C.)) of platinum metal as simple substance, the measured values of the thin films of the present embodiments are somewhat larger, but is deemed to be low as the resistance values of the platinum thin films prepared by performing film formation at low temperatures.

As has been revealed from the above-described results of the film formation test, the platinum complexes according to the respective embodiments enable, by using hydrogen as reaction gas, the film formation at a temperature as low as 200° C. Although these platinum complexes are stable compounds at room temperature, these platinum complexes have the properties of quickly undergoing decomposition reaction by heating and easily depositing metallic platinum, and hence are suitable for the production of metal thin films by the CVD method. As has also been revealed, the organic components (hexadiene as a ligand and methane) produced by the thermal decomposition of the platinum complexes are all low in boiling point, and are evaporated and diffuse quickly under the reduced pressure condition for performing film formation, and hence are not incorporated into the deposited metal thin films so as to enable the fabrication of pure metal film.

As described above, the platinum complexes according to the respective embodiments all enabled the formation of platinum thin films under all the conditions; however, the film formability at low temperatures is satisfactory in the order of HDMP<Me-MHDMP<2Me-MHDMP. The specific resistance of the platinum thin film was observed to have a tendency represented by HDMP>Me-MHDMP>2Me-MHDMP. As described on the results of the TG-DTA measurement, this is because as the molecular weight of the complex increases, the weight loss initiation temperature and the weight loss completion temperature become lower so as to facilitate the thermal decomposition, and thus, the film formation is enabled at lower temperatures and the specific resistance is also decreased.

Comparative Examples

For comparison with the platinum complexes according to the foregoing respective embodiments, bis(acetylacetonato)platinum(II) complex, a conventional platinum compound, was subjected to the evaluation of physical properties and the formation of a thin film.

First, a TG-DTA measurement was performed. In the case of bis(acetylacetonato)platinum(II) complex, the weight loss starts from around 150° C., the loss magnitude drastically increases at around 225° C., and the weight loss came to an end at 245° C. In this case, the weight loss corresponding to 99.96% of the initial weight occurred. This shows that the sample was evaporated (sublimed) completely without undergoing thermal decomposition (deposition of platinum) and the sample is stably present up to 245° C. without being thermally decomposed in an argon atmosphere. From a comparison of this result with the case of HDMP (the completion of the heating decomposition at 150° C.), for forming a film by using bis(acetylacetonato)platinum(II) complex, it is anticipated that a heating temperature higher by 100° C. or more than the heating temperature for HDMP is required.

Next, by using bis(acetylacetonato)platinum(II) complex, a formation of a platinum thin film was tried. The film formation conditions were the same as in the present embodiments except that the substrate temperature was set at 350° C. However, in this film formation test, bis(acetylacetonato)platinum(II) complex was evaporated, but was not decomposed on the substrate and no platinum thin film was formed. It has been verified that the platinum compound does not enable the film formation at a temperature of 350° C. or lower, contrary to the present embodiments.

By using cyclopentadienyl trimethylplatinum(IV complex as a conventional platinum compound, a formation of a platinum thin film was tried. The film formation conditions were such that the sample heating temperature was set at 25° C., the substrate temperature was set at 300° C., and 10 sccm of hydrogen was used as the carrier gas and the reaction gas. The pressure at the time of film formation is 65 Pa. Under the conditions, the film formation was tried for 30 minutes, but no formation of a metal film on the substrate was recognized.

As described above, the platinum complexes of the present embodiments are, in contrast to conventional platinum compounds, enable the formation of platinum thin films at low temperatures. The platinum complexes of the present embodiments are stable at room temperature against air, humidity and light, and can be stored over a long period of time. As the carrier gas used for the vaporization of the platinum complexes, argon or nitrogen, which are nontoxic and inexpensive, can be used. Moreover, the platinum complexes of the present embodiments generate no toxic substance when the film formation is performed, and hence can be regarded as platinum compounds for CVD, easy in handling and excellent in practicability.

INDUSTRIAL APPLICABILITY

The platinum complex according to the present invention has a high vapor pressure and a low decomposition temperature, and hence can form a high-precision platinum thin film at a low temperature. The present invention is particularly effective for film formation on spatial structure, and is useful for the formation of a platinum film, for example, on the solid-type electrode of an FET, having a three-dimensional structure.

What is claimed is:
1. A chemical vapor deposition method for forming a platinum thin film or a platinum compound thin film, comprising the steps of vaporizing an organoplatinum compound to be a raw material compound to prepare a reaction gas, introducing the resulting reaction gas onto the surface of a substrate, and decomposing the organoplatinum compound to deposit platinum, wherein said method uses, as the organoplatinum compound, the organoplatinum compound,
which is represented by the following formula and includes a divalent platinum atom, and hexadiene or a hexadiene derivative and alkyl anions coordinated to the divalent platinum atom, and decomposes the organoplatinum compound

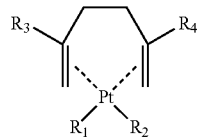

Formula 1 wherein at least either of the substituents $R_1$ and $R_2$ is any one of a methyl group, an ethyl group and a propyl group; $R_1$ and $R_2$ may be different from each other; $R_3$ and $R_4$ are each a hydrogen atom or an alkyl group; and $R_3$ and $R_4$ may be different from each other.

2. The chemical vapor deposition method according to claim 1, wherein the reaction atmosphere for decomposing the organoplatinum compound is a reducing atmosphere.

3. The chemical vapor deposition method according to claim 2, wherein as the reducing atmosphere, hydrogen or ammonia is introduced.

4. The chemical vapor deposition method according to claim 1, wherein at least either of the substituents $R_3$ and $R_4$ is a methyl group.

5. The chemical vapor deposition method according to claim 1, wherein the substituents $R_1$ and $R_2$ are each a methyl group and the substituents $R_3$ and $R_4$ are each a hydrogen atom.

6. The chemical vapor deposition method according to claim 1, wherein $R_1$ and $R_2$ are the same, and at least either of the substituents $R_3$ and $R_4$ is a methyl group.

7. The chemical vapor deposition method according to claim 2, wherein the substituents $R_1$ and $R_2$ are each a methyl group and the substituents $R_3$ and $R_4$ are each a hydrogen atom.

8. The chemical vapor deposition method according to claim 3, wherein the substituents $R_1$ and $R_2$ are each a methyl group and the substituents $R_3$ and $R_4$ are each a hydrogen atom.

9. The chemical vapor deposition method according to claim 2, wherein $R_1$ and $R_2$ are the same, and at least either of the substituents $R_3$ and $R_4$ is a methyl group.

10. The chemical vapor deposition method according to claim 3, wherein $R_1$ and $R_2$ are the same, and at least either of the substituents $R_3$ and $R_4$ is a methyl group.

* * * * *